(12) United States Patent
Major

(10) Patent No.: US 8,176,925 B2
(45) Date of Patent: *May 15, 2012

(54) DENTAL FLOSS TOOL DEVICE AND METHOD

(76) Inventor: Mark L. Major, Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/653,286

(22) Filed: Dec. 11, 2009

(65) Prior Publication Data

US 2010/0095978 A1   Apr. 22, 2010

Related U.S. Application Data

(63) Continuation of application No. 11/143,504, filed on Jun. 2, 2005, now Pat. No. 7,631,650.

(60) Provisional application No. 60/576,538, filed on Jun. 2, 2004, provisional application No. 60/585,244, filed on Jul. 2, 2004.

(51) Int. Cl.
 *A61C 15/00* (2006.01)
(52) U.S. Cl. ............... 132/323
(58) Field of Classification Search ........... 132/322–329
 See application file for complete search history.

(56) References Cited

U.S. PATENT DOCUMENTS 5,762,078 A * 6/1998 Zebuhr .......... 132/322
6,363,949 B1 * 4/2002 Brown .......... 132/325

* cited by examiner

*Primary Examiner* — Rachel Steitz

(57) ABSTRACT

A device to aid in flossing teeth including a jaw hook body, a pair of floss retaining projections on one end of the jaw hook body, and a grip handle at an opposite end of the jaw hook body. The grip handle may be a closed loop, an open loop, a padded structure, a pivoting structure, a decorative structure, a structure for holding the tool upright on a surface, or some combination of these features.

9 Claims, 5 Drawing Sheets

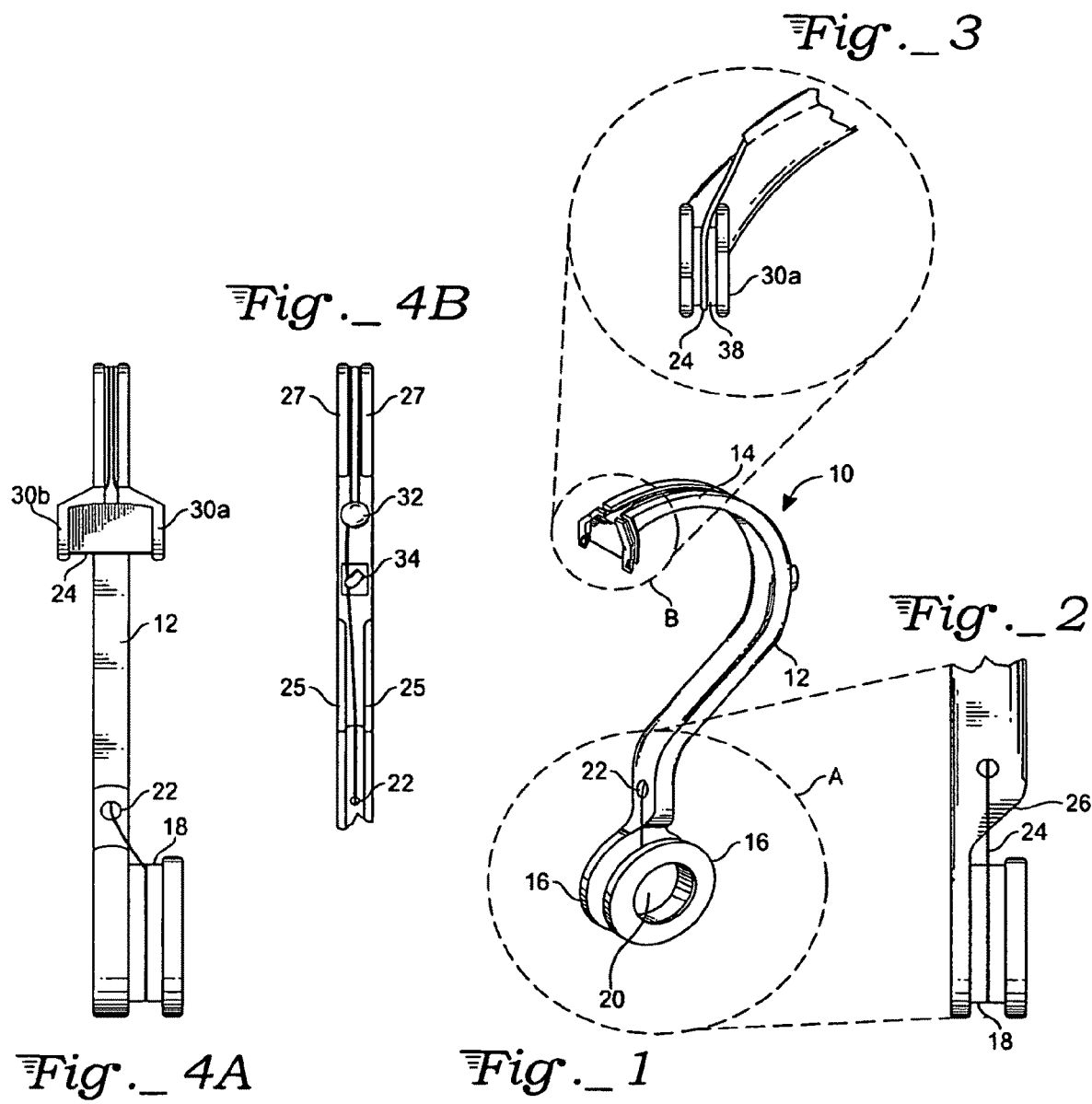

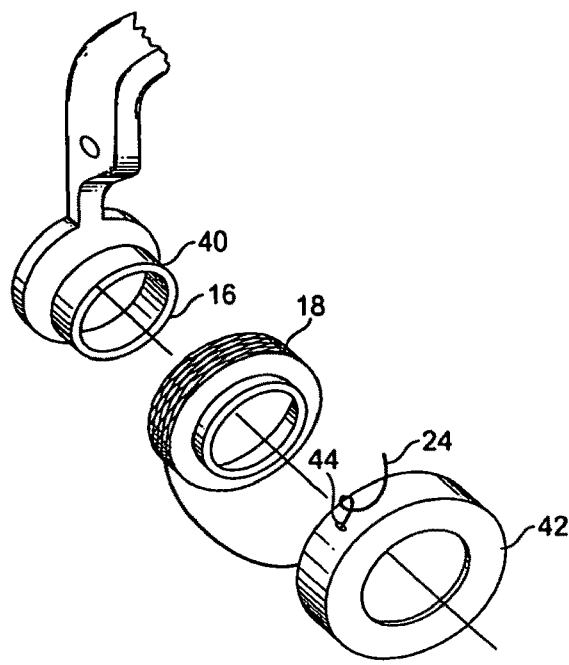
Fig._5
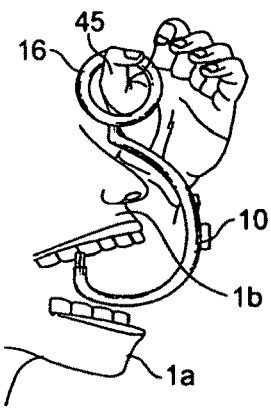
Fig._6
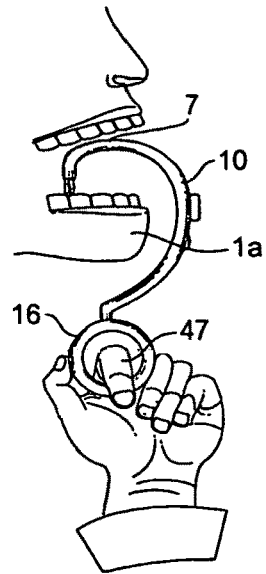
Fig._7
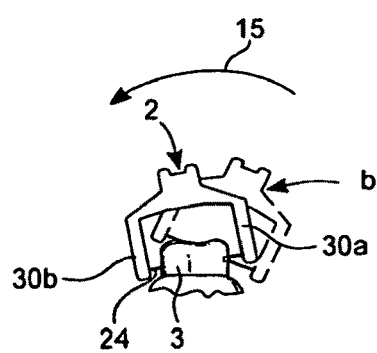
Fig._8

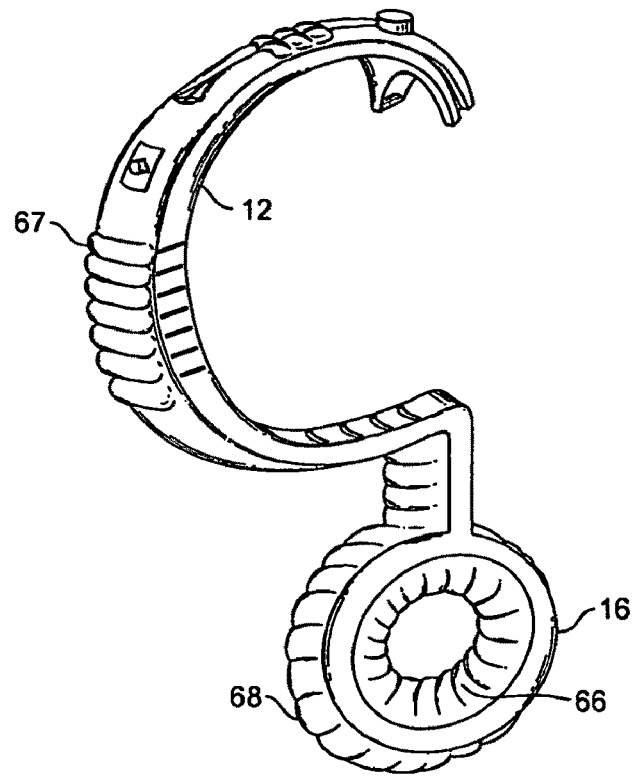
Fig._ 11
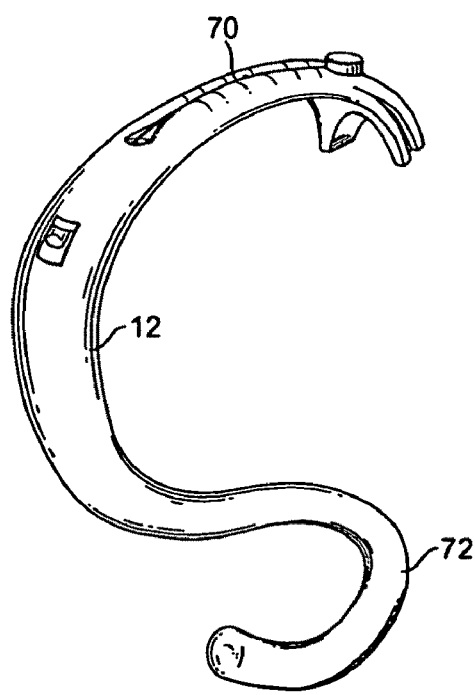
Fig._ 12

DENTAL FLOSS TOOL DEVICE AND METHOD

CROSS-REFERENCE TO RELATED APPLICATIONS

The present application is a continuation and claims the priority and benefit of U.S. patent application Ser. No. 11/143,504, filed on Jun. 2, 2005, now U.S. Pat. No. 7,631,650 and titled "DENTAL FLOSS TOOL DEVICE AND METHOD," which in turn claims priority and benefit to U.S. provisional patent application No. 60/576,538, filed on Jun. 2, 2004, and titled "Dental Floss Holder," and U.S. provisional patent application No. 60/585,244, filed on Jul. 2, 2004, and titled "Dental Floss Holder." The disclosures of all of the above U.S. patent applications are incorporated by reference herein in their entirety.

TECHNICAL FIELD

The present device relates to a device and method for using dental floss.

BACKGROUND ART

Flossing between teeth is recommended for proper dental hygiene. However, the use of dental floss may be difficult for some users. This problem is enhanced for users with poor finger dexterity, users who are missing fingers, or users that have had other hand disabilities.

A number of prior devices have been created to aid in flossing. For example, U.S. Pat. No. 3,858,594 discloses a dental floss holder that dispenses floss through a hole in the main body of the device. A cavity within the body of the device holds a spool, which dispenses floss to this hole. The body has a curved shape terminating in a pair of forked tines extending from the device body and spaced far enough apart to allow user to introduce a length of floss into the user's mouth and between the user's teeth. The gap has to be sufficiently wide such that the tines can fit between the front and back of a user's teeth. These tines extend sufficiently far from the device's body and are curved to allow reaching teeth at the back of the mouth without inserting the user's hand into the mouth. The floss is strung by the side of the curved tool body between the two tines and along another side of the tool body to a retaining latch. When the user flosses with this device, the user's thumb grips both the floss and the tool, thereby pressing the floss against the side of the tool and creating tension in the floss.

U.S. Pat. No. 4,807,651 discloses a rigid sickle-shaped tool body having a finger handle at one end of the tool body. The floss is strung between projections on the device body. The projections are adapted to allow multiple strands or loops of floss to be held between a gap on the tool. The handle of the tool is a trigger-like ring through which a user inserts an index finder. The user's thumb rests on the top of the tool, holding a dental floss puller, and the user's middle finger is positioned below the device.

These prior art devices require that a user push the tool to floss between teeth. This pushing may be awkward and cumbersome for some users. Such motion requires at least gripping the floss and device with a number of fingers.

An alternative to the gripping-type devices and method is needed.

SUMMARY OF THE INVENTION

The present device includes a jaw hook body having a set of spaced dental floss holding projections at a first end and a grip handle at the second end of the jaw hook body. A floss retainer is positioned on the tool such that dental floss strung between the set of spaced dental floss holding projections may be secured on the floss retainer. This tool allows the user to grip the grip handle with one or more curled fingers and, using an essentially vertical motion, pull the floss between the teeth. This device may include a spool on the handle or in the body of the tool for holding a spool of dental floss. This spool retainer may have a cover protecting the dental floss from contamination. The body of the tool may also include a floss cutter located on the tool body. The grip handle may include specialized features, for example including a thumb grip or rubberized inner surface. Grooves along the body of the tool in the projections for holding the floss may aid in ensuring that the floss is retained in the tool. The method of using this tool includes applying a vertical (up and down) force above or below a user's jaw. The device may be rocked during use to facilitate the cleaning of the space between teeth. A bite surface on the tool's body may aid in applying the desired force. This pulling motion may be easier than the pushing motion required in prior devices.

BRIEF DESCRIPTION OF THE DRAWINGS

FIG. 1 is a side perspective view of an embodiment of the floss aid tool.

FIG. 2 is a front view of detail A in FIG. 1, showing the handle/spool.

FIG. 3 is a detailed view of the projections shown in B of FIG. 1.

FIG. 4A is a front view of the floss aid tool of FIG. 1.

FIG. 4B is a partial back view of the floss aid tool of FIG. 1.

FIG. 5 is an exploded view showing the spool of dental floss.

FIG. 6 is a side view of the floss aid tool in use flossing the teeth in a user's upper jaw.

FIG. 7 is a side view of a user flossing the teeth of the user's lower jaw.

FIG. 8 is a side view illustrating the motion of the floss holding projections of the floss aid tool in use.

FIG. 11 is a side perspective view of an alternative embodiment of the tool, including rubberized gripping surfaces.

FIG. 12 is a side view of an alternative embodiment of the tool including an open loop grip.

DETAILED DESCRIPTION

Figure 9:
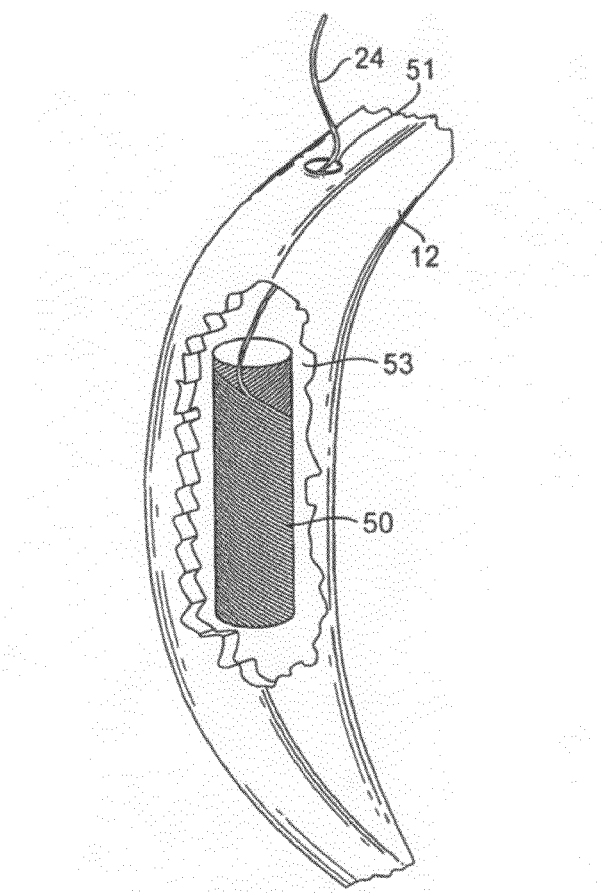
FIG. 9 is a perspective view of the tool body showing a cut-away with an internal compartment a dental floss spool.

With reference to FIG. 1, the dental floss tool 10 is shown including a tool body 12 having a top section 14 at one end of the tool body 12 and a handle 16 at an opposite end of the tool body 12. The curved, generally half-circular shape of the tool body 12 allows a user to insert the tool into the user's mouth. Floss secured between projections at one end of the tool body 12 is able to reach even the back teeth in the user's mouth. This shape is referred to as a "jaw hook body". This body generally has a question mark shape.

The handle 16 includes a through hole 20 through which a user can place one or more fingers. In this embodiment, a spool of dental floss 18 may be mounted on handle 16. As show in FIG. 2, spool 18 holds floss 24. A recessed surface 26 allows simplified access to floss spools at this location. Returning to FIG. 1, the floss fed from spool 18 is fed through hole 22 on the tool body.

With reference to FIG. 3, the head of the tool, detail B from FIG. 1, shows the floss 24 on projection 30A. A groove 38 on projection 30A retains floss 24. These grooves aid to ensure that the floss remains on projection 30A during flossing. Other structures, such as a hook or loop on the projection, could also be used.

With reference to FIG. 4A, the front to the tool shows the floss 24 being fed from spool 18 through hole 22. The view in FIG. 4B shows the floss 24 emerging from hole 22 and being positioned along the body of the tool in a handle groove defined by ridges 25. The floss moves past additional ridges 27 in a floss retaining groove to the projections forming the head of the tool. The floss on the return path is wound around a floss retainer 32. Before being wound around floss retainer 32, the floss may be cut by floss cutter 34. Retainer 32 may be a clip, knob or other floss retaining structure. In some embodiments, the floss may be first retained by floss retainer 32 prior to the floss being fed to the head of the tool. This may allow greater tension to be placed on the floss.

In FIG. 4A, the head of the tool is shown including spaced projections 30A and 30B. Extending between projections 30A and 30B is dental floss 24. The projections are spaced with sufficiently wide spacing such that the projections may be positioned on either side of two teeth of a user.

The various designs shown by the various embodiments allow a user to apply a pulling force to floss, using only a single finger or thumb in some embodiments. Even using a single finger, a significant improvement in control of the floss aid is achieved. This tool may be especially useful to people with limited manual dexterity.

An embodiment of the handle with a spool retainer is illustrated in FIG. 5, which shows handle 16 including a spool mount area 40. A replacement spool of dental floss 18 may be positioned over retaining area 40. One end of dental floss 24 is fed through hole 44 on snap on cover 42. Cover 42 may be securely snapped over handle 16 and either functionally retained or retained on latches. This cover prevents tangling of the dental floss and allows the dental floss to be kept clean during storage of the tool. Given that many commercially available dental flosses are sold on similar types of spools having known spool dimensions, this particular design allows such commercially available dental floss to be used in the present tool.

In FIG. 6, a user is illustrated using tool 10. The tool is positioned such that teeth in a user's jaw 1B may be cleaned. A user's lower jaw 1A may be subsequently cleaned. A user's thumb 45 extends through handle 16. Handle 16 may be designed such that a single finger or multiple fingers may be extended through the handle.

With reference to FIG. 7, the teeth of lower jaw 1A are shown being flossed by the tool 10. Finger 47 is extended through handle 16. The body of the tool presents a surface 7 onto which a user might bite down to help control motion of the tool and to provide additional leverage for inserting the floss between teeth. It may be desirable to rubberize surface 7 to increase comfort during such a bite down procedure. The tool may be used with a up and down motion or in rocking side to side.

With reference to FIG. 8, such a rocking motion is illustrated. Arrow 5 indicates the direction of this rocking motion. Tooth 3 is cleaned on one side by floss 24. Projections 30A and 30B are on the front and back side of the tooth 3, respectively. When moving between positions A and B, the floss is scraped between tooth 3 and a adjacent tooth, aiding in the cleaning of the space between teeth. Such a rocking motion may help to both clean the teeth and to remove or insert the floss from between teeth as the floss is moved from tooth to tooth during a flossing process. This rocking motion provides additional leverage.

With reference to FIG. 9, a device body 12 is shown having a internal cavity 53 in which a spool of floss 50 is placed. The floss 24 is fed through opening 51 in the body. A cover (not shown) provides access to this internal cavity 53.

Figure 10:
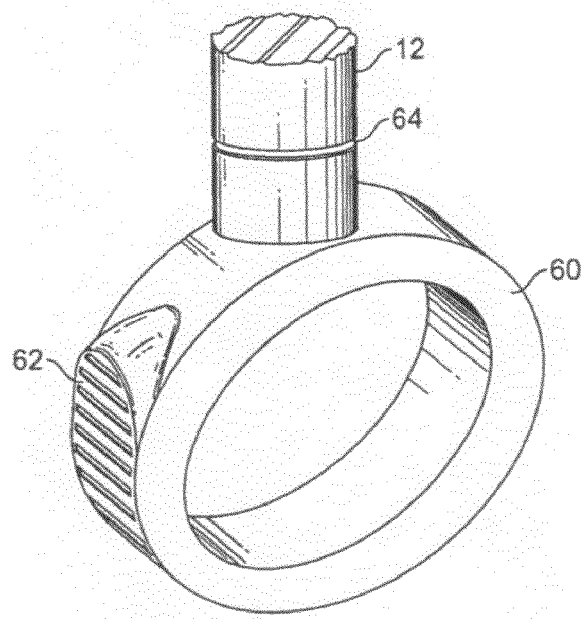
FIG. 10 is a side perspective view of an alternative handle including a thumb grip.

With reference to FIG. 10, an alternative handle is shown including a handle grip 60 having a thumb grip 62. This embodiment also includes a pivot attachment to the tool body 12 at pivot 64. The pivot attachment could allow 100 degree rotation of the handle.

With reference to FIG. 11, the handle 16 is shown having an internal rubberized surface 66. This surface may aid in the user in moving the tool in the pivoting motion shown in FIG. 8. In addition, the top rubberized surface may act as a biting surface, as described above. The exterior surface 68 of handle 16 may also be rubberized, as may be the surface 67 of tool body 12.

Another alternative embodiment of the device is shown in FIG. 12 where tool body 12 is attached at its lower end to a open loop handle 72. In this version, an amount of floss is dispensed from a floss spool within a cavity inside body 12. On body 12, the floss is held in a groove 70.

Figure 13:
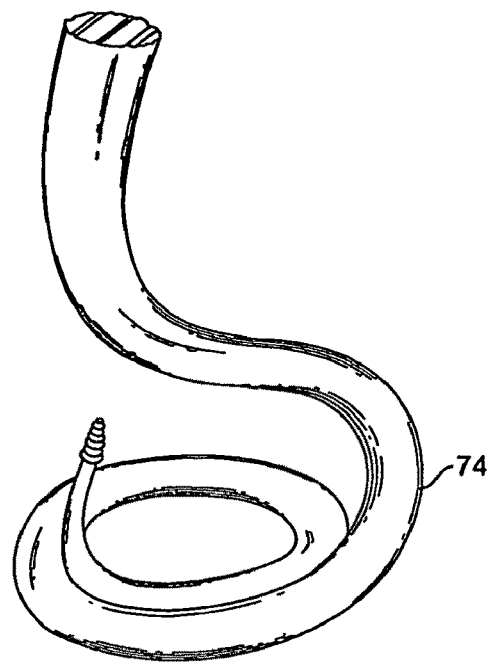
FIG. 13 is a side view of an alternative grip which is freestanding.
Figure 14:
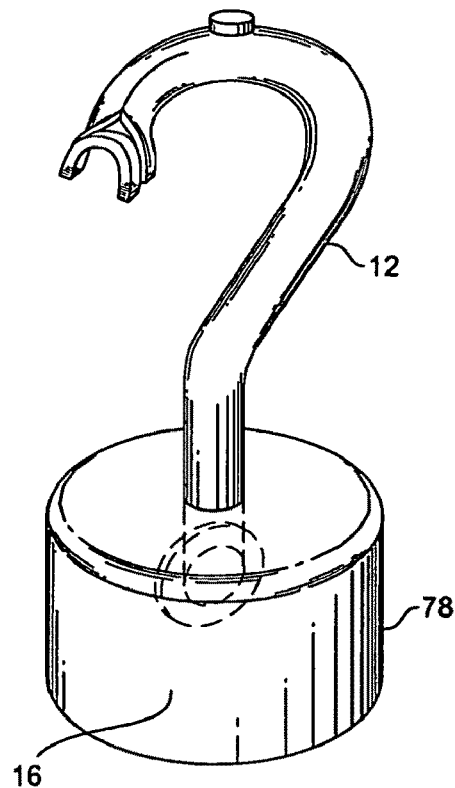
FIG. 14 is a side view of an alternative grip embodiment.

Alternative handles are shown in FIGS. 13 and 14. FIG. 13 includes a handle positioned such that handle 74 rests flat on a surface when the device is not in use. This may be useful for a possible display of the handle.

FIG. 14 shows tool body 12 joined to handle 16 which is covered by cap 78. This provides an attractive and whimsical aesthetic appearance to the device, while also providing a shield from germs for the user's hand during use. A number of alternative decorative designs of the handle and/or the body of the device may be used. For example, animal shapes, toy images, moon shapes, a scorpion shape, or a banana shape could all be adapted to the device body and/or the grip.

What is claimed is:

1. A dental floss tool comprising:
   a head having a first end and a second end, the first end able to secure a length of floss; and
   a handle having a curved portion and a grip portion,
      a first end of the curved portion attached to the second end of the head and extending away from the head to form an open aperture,
      the grip portion connected to a second end of the curved portion, the head intersecting a line extending along an axis of the grip portion,
      the open aperture having a shape to allow the head to be positioned within a mouth of a user and apply floss to a tooth of the user while the grip portion of the handle is positioned directly outside the mouth and underneath a jaw of the user, the tooth and the jaw of the user intersecting the line extending along the axis of the grip portion,
      the head configured to displace the length of floss between the teeth of the user in a first direction when a pulling force is applied to the grip portion parallel to the line extending along the axis of the grip portion.

2. The tool of claim 1, further comprising a length of floss secured to the first end of the head.

3. The tool of claim 2, further comprising a spool coupled to the grip portion and the length of floss.

4. The tool of claim 2, wherein the floss intersects the line extending along the axis of the grip portion at a point between second end of the head and the grip portion.

5. The tool of claim 1, wherein the handle includes an aperture.

6. The tool of claim 5, wherein the aperture is configured to receive a finger of a user.

7. The tool of claim 1, wherein the handle includes a hook configured to receive a finger of a user.

8. The tool of claim 1, wherein the head is permanently attached to the handle.

9. The tool of claim 1, wherein the head is removable from the handle.

\* \* \* \* \*